United States Patent [19]

Hofman

[11] Patent Number: 5,682,149
[45] Date of Patent: Oct. 28, 1997

[54] MEASURING DEVICE FOR THE WIRE-FREE MEASUREMENT OF TEMPERATURE

[75] Inventor: Hendrik Hofman, Marknesse, Netherlands

[73] Assignee: Idento Electronics B.V., Marknesse, Netherlands

[21] Appl. No.: 649,016

[22] Filed: May 16, 1996

[30] Foreign Application Priority Data

May 16, 1996 [NL] Netherlands .................. 1000369

[51] Int. Cl.⁶ .................................................. G08C 19/12
[52] U.S. Cl. .......................... 340/870.17; 340/870.18; 340/870.26
[58] Field of Search .............. 340/870.16, 870.17, 340/870.18, 870.26, 870.3, 870.31, 825.54, 825.73; 455/41, 69

[56] References Cited

U.S. PATENT DOCUMENTS 4,075,632  2/1978  Baldwin et al. .................. 342/51
5,252,962  10/1993  Urbas et al. .................. 340/870.17

FOREIGN PATENT DOCUMENTS 36 10960  10/1987  Germany .
41 25 746  2/1992  Germany .
40 34 019  7/1992  Germany .

*Primary Examiner*—Jeffery Hofsass
*Assistant Examiner*—Andrew Hill
*Attorney, Agent, or Firm*—Burns, Doane, Swecker & Mathis, L.L.P.

[57] ABSTRACT

The invention relates to a measuring device for the wire-free measurement of temperatures, in particular for the measurement of the body temperature of animals. A transponder is injected as a probe in each animal with the aid of a hollow needle, which is supplied wire-free by a transmitter/receiver and which modulates the interrogation field with two or more abruptly changing tones in a cyclic sequence.

The time duration of the tones as well as the frequency of the tones contain the desired information in coded form.

By monitoring individually and continuously the body temperature of useful and/or breeding animals in the animal shed or on the pasture, it is possible to detect in time completely automatically the symptoms of an animal becoming ill and appropriate measures can be taken in order to keep the costs as low as possible in the animal husbandry business.

4 Claims, 4 Drawing Sheets

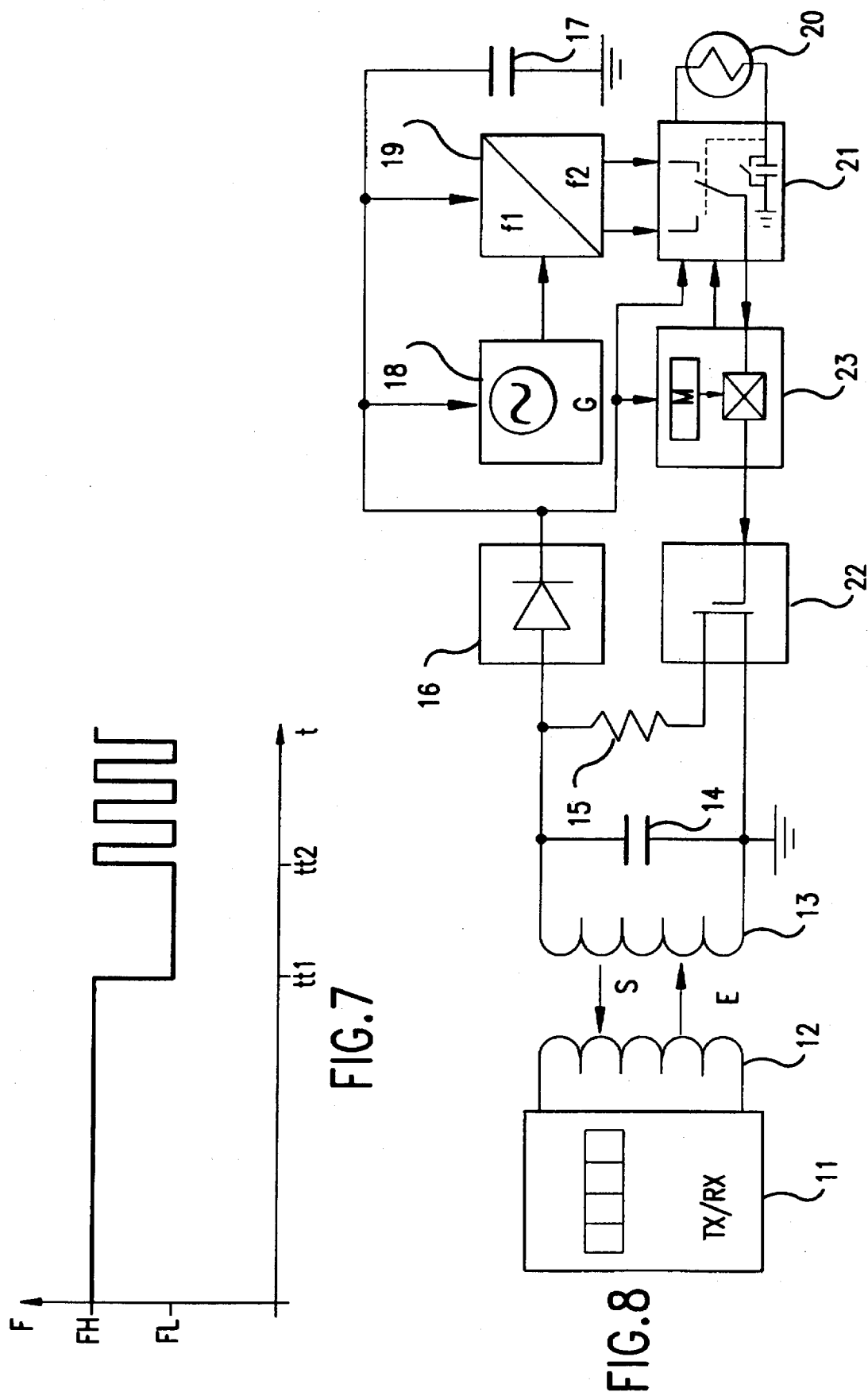

MEASURING DEVICE FOR THE WIRE-FREE MEASUREMENT OF TEMPERATURE

BACKGROUND AND SUMMARY

The invention relates to a measuring device for the wire-free measurement of temperatures.

The device lends itself to monitoring the body temperature of animals, for example in the animal shed, virtually continuously and, if the body temperature deviates from the normal temperature for the animal concerned, to taking appropriate measures, possibly completely automatically.

The device is especially suitable for the timely detection of the onset of diseases in useful animals and breeding animals if their becoming ill is associated, for example, with a marked increase in the body temperature.

The device is furthermore suitable, in particular, for automating the care of animals because, for example if a need for care is detected by a microprocessor-controlled processing unit of the measuring device, the outbreak of a disease can already be prevented during feeding in the initial stage by a controlled addition of approprate drugs to the quantity of feed.

The invention proceeds from the problem of monitoring the body temperature of animals individually and continuously, for example in the animal shed, in order thereby to detect even the onset of diseases in good time and to be able to take appropriate measures, possibly completely automatically, in order thereby to keep the costs as low as possible in the animal husbandry business.

This problem is solved in the case of the measuring device for the wire-free measurement of temperatures by a measurement probe, including one or more extremely miniaturized transponder (TRS) which are encapsulated in a cylindrical glass tube hermetically sealed at both ends and of very small diameter, which are to be injected with the aid of a hollow needle and which have a built-in sensor element, the injectable transponder (TRS) converting the temperature to be measured in each case into an electrical signal and a transmitter/receiver (TRX) whose transmitting section of the transmitting and receiving unit generates an interrogation field with the aid of a transmitting/receiving coil and thereby makes available the operating power required for supplying the injectable transponder and whose receiving section of the sending and receiving unit receives the signals generated by the TRS and processes them in a suitable manner, the TRS having, for its part, a transponder coil which forms, together with a capacitor, a resonant circuit and, as a result of the interaction of said resonant circuit with the electromagnetic interrogation field, a wire-free link is produced between the TRS and the transmitting/receiving coil and consequently with the TRX, the TRS modulating (in contrast to digital methods) in an essentially analog manner, without needing an additional transmitter module, the electromagnetic interrogation field by means of the variation, proportional to the signal information, in the operating energy consumed, characterized in that the TRS modulates the interrogation field with two or more discrete low-frequency tones alternating with one another in an analog manner in a cyclic sequence, only a single tone being produced in each case for a certain time duration, the frequency of which tone changes abruptly after the expiry of said specific time duration, the time duration of the respective audio signal being a measure of the temperature measured. Advantageous further developments of the invention are described in detail below.

The invention opens up the possibility of carrying out in a simple manner a completely automatic monitoring of the body temperature, and consequently of the state of health, of animals when they appear in the normal course of events several times a day in the vicinity of the automatic feed units. As a result, the onset of diseases can already be detected in the initial stage and treated in good time.

The advantages achieved by the invention are especially that there is the possibility of central monitoring and, consequently, a smaller number of caring staff will be needed since the special care required in the case of diseases of the useful animals and breeding animals concerned is very staff-intensive and can then be limited to those animals which have a markedly increased body temperature as an indicator of the onset of, or already advanced, serious disease. A manual temperature measurement, for example in the anus of the sick animal, which may adversely effect its well-being does not also have to be carried out separately, which is to be regarded as a further advantage.

Another advantage achieved by the invention is that, as a result of the use at very low cost of electronic computers in the method of measuring and monitoring, the temperature peak, which is critical for the animals concerned, can also be detected even in the incipient phase without additional monitoring by the caring staff (for example, during the night or at weekends) and, for example, automatic feed additions in the form of appropriate drugs (for example, antibiotics) can therefore be made as preliminary countermeasures.

Measuring devices for the wire-free measurement of the body temperature of an animal with the aid of a transponder are disclosed per se, for example in U.S. Pat. No. 4,075,632, DE-C-3 219 558, DE-C-3 932 428 and EP-B-0 395 188.

In contrast to the measuring devices described therein and comprising transponders, the transponder employed in the present measuring device is miniaturized to such an extent that it is hermetically encapsulated in a small, cylindrical glass tube, sealed at both ends, of only a few millimetres in diameter and is injected into the tissue of the animal with the aid of a hollow needle.

In order, therefore, to have an adequate field strength even at large distances between the animal and the transmitting coil to be able to interrogate the transponder, the transmitter must supply a sufficiently high transmitting power.

As a result of the continual movement of the animal, however, the distance between the transponder and the transmitting coil also varies continuously, and the voltage induced in the transponder consequently varies considerably. If a voltage regulator were to be placed in the transponder, with the miniaturized structure outlined for the transponder, the heat loss developed in such a voltage regulator could not be dissipated outwards quickly enough and, as a result, could influence the temperature-sensitive element in an incorrect manner.

As a result of abruptly switching the sound signal cyclically, the transponder signal can be identified unambiguously by the measuring device and said signal cannot be confused with interference signals which occur in the same frequency range and which generally manifest themselves in unmodulated form and at constant amplitude.

It is pointed out that an implantable transponder which has been developed solely to identify an animal, in particular a freshwater fish, is disclosed in EP 0 258 415. This miniature transponder can be injected with the aid of a hollow needle. The parasitic capacitances have been used in the miniaturization of the transponder circuit, as a result of which the dimensions can be as small as possible. A temperature measurement is not possible therewith, nor intended.

BRIEF DESCRIPTION OF THE DRAWINGS

To explain the measuring device according to the invention, some embodiments of the measuring device are shown in the drawing by way of example.

FIG. 7 shows, for the purpose of explanation, a typical pattern of the sequence of alternating tones obtained as a signal from the transponder at a certain, but constant temperature, the sequence of the alternating tones being asymmetrical and an additional code being inserted;

FIG. 8 is an exemplary embodiment of the block diagram of the internal structure of a transponder for temperature measurement having an additional unit for obtaining an identification code.

DETAILED DESCRIPTION

Figure 1:
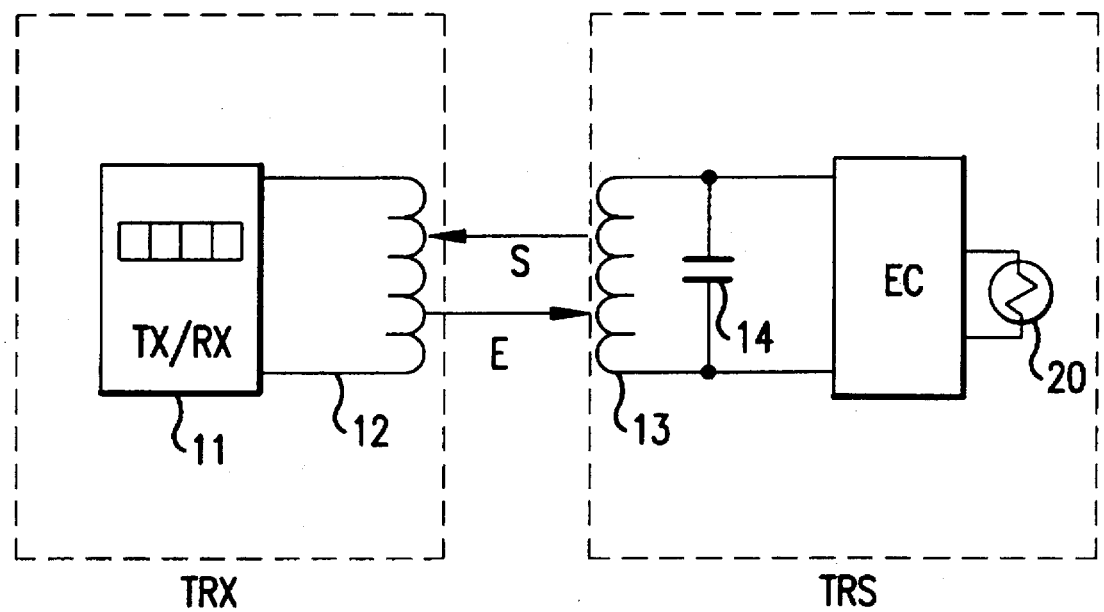
FIG. 1 shows a diagrammatic arrangement of the separate components of the measuring device according to the invention.

The circuit depicted in FIG. 1 of the separate components of the measuring device shows, on the one hand, the transceiver, or transmitter/receiver, TRX and, on the other hand, the transponder TRS. The transmitter/receiver TRX supplies, inter alia, the transponder TRS with the power E which the latter needs for its intended operation. The transponder (TRS) supplies the transmitter/receiver TRX with the signals S which contain the desired information in coded form. The transmitter/receiver TRX comprises a simultaneously operated transmitting and receiving unit 11 having a transmitter which supplies the transmitting/receiving coil 12 with an unmodulated permanent signal, adjustable for power, in the region of approximately 150 kHz. As a result, an electromagnetic interrogation field having the frequency of the unmodulated permanent signal is built up in the region of the transmitting/receiving coil 12. Said electromagnetic interrogation field supplies the transponder TRS situated in the field with the supply power E required for operation. The transponder TRS has a resonant circuit which is made up of the transponder coil 13 and a separate capacitor 14 and which, with regard to its resonance frequency, is tuned to the unmodulated permanent signal emitted by the transmitter/receiver TRX. As a result of the magnetic coupling between the transmitting/receiving coil 12, on the one hand, and the transponder coil 13, on the other hand, there is induced in the resonant circuit formed from the transponder coil 13 and the capacitor 14 an alternating voltage from which the transponder TRS makes available its operating voltage Vdd with the aid of its electronic circuit EC, which is still to be described later.

The level of the induced voltage value depends directly on the level of the value of the power E drawn from the electromagnetic interrogation field. This value is linked in turn to the degree of coupling between the transmitting/receiving coil 12, on the one hand, and the transponder coil 13, on the other hand. As the distance between the coils increases, the degree of coupling decreases.

While the transmitter/receiver TRX is, as a rule, arranged in a stationary fashion, the transponder TRS is implanted, in accordance with its purpose, in an animal with the aid of a hollow needle and consequently moves concomitantly with the animal. If the animal which is carrying the transponder TRS around with it approaches the transmitting/receiving coil 12, the transponder TRS draws increasingly more power from the electromagnetic interrogation field built up by the transmitting/receiving coil 12 because of the increasing coupling between the coils as the distance becomes smaller.

As soon as the value of the power E drawn from the electromagnetic interrogation field has reached a level which is sufficient to operate the transponder TRS in accordance with the purpose, the transponder TRS processes the temperature values determined by means of a thermistor 20 (as the actual temperature-determining element) and in turn generates suitable signals S with which the electromagnetic interrogation field generated by the transmitter/receiver TRX is modulated. The signals S generated in this way by the transponder TRS, are picked up by the transmitting/receiving coil 12 and red to the receiver in the transmitting and receiving unit present in the transmitter/receiver TRX and processed in accordance with their purpose.

Figure 2:
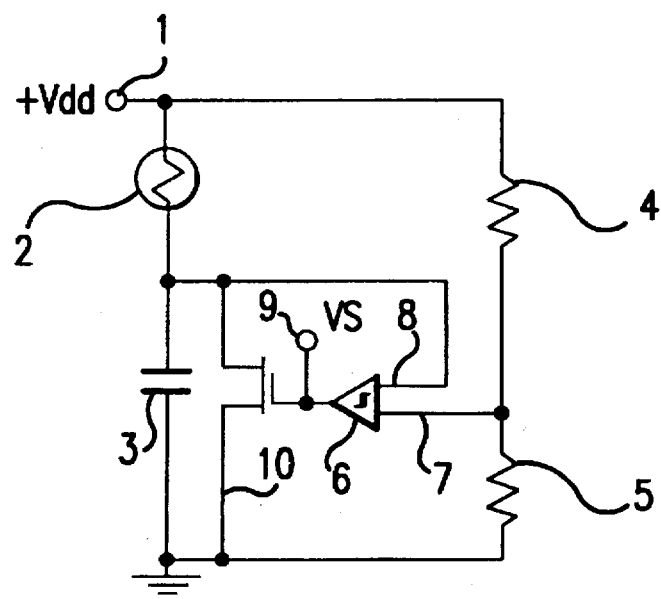
FIG. 2 shows an exemplary embodiment of the circuit of the time-base generator used for the temperature measurement.

The exemplary embodiment shown in FIG. 2 of the circuit of a suitable time-base generator used in the transponder TRS for the temperature measurement demonstrates how a very accurate temperature measurement can be carried out effectively and efficiently with the aid of the simplest analog technology.

Present at the input terminal 1 is an operating voltage Vdd which is positive with respect to the operating earth. The prevailing capacitor voltage Vc arrives at the input 8 of a comparator 6. Generated across the voltage divider formed from a resistor 4 connected to the operating voltage Vdd and a resistor 5 connected to the operating earth is a reference voltage Vr which is connected to the other input 7 of the comparator 6. As long as the voltage across the capacitor Vc is less than said reference voltage Vr, the output voltage Vs of the comparator 6 is at a level which is not sufficient to drive the blocked field-effect transistor 10. As soon as the voltage across the capacitor Vc reaches the value of the reference voltage Vr, the output signal Vs of the comparator 6 varies in such a way that the field-effect transistor 10 abruptly becomes conducting and, as a result of the internal resistance becoming infinitesimally small, the capacitor 3 discharges equally abruptly. As a result, the voltage Vc across the capacitor 3 again drops below the value of the reference voltage Vr and the field-effect transistor 10 is again blocked.

This process repeats itself in a cyclic sequence. A sawtooth-type time-base voltage appears at the output terminal 9. In the case of a constant operating voltage Vdd, the repetition frequency of said sawtooth-type voltage then depends solely and exclusively on the value of the resistance of the thermistor 2 and thus directly on the temperature.

Figure 3:
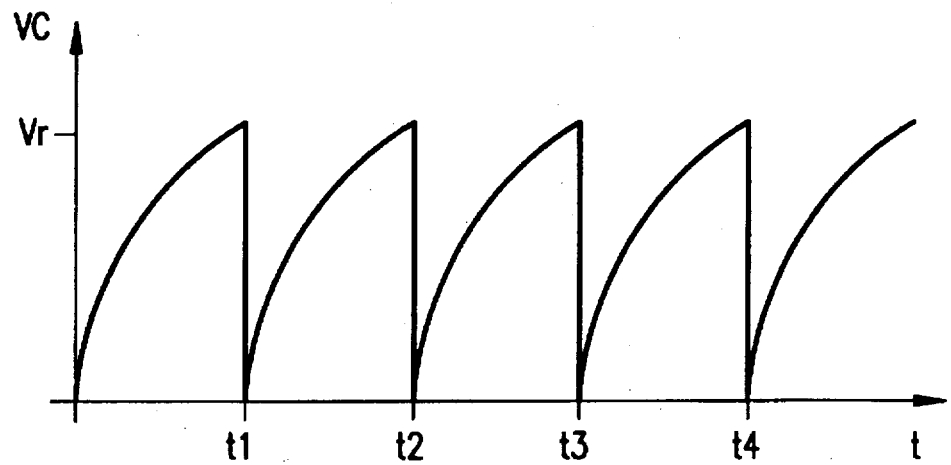
FIG. 3 shows, for the purpose of illustration, in particular, the variation with time of the voltage which is generated by the time-base generator and which is temperature-dependent.

For the purpose of explanation, FIG. 3 shows, by way of example, the variation with time of the voltage which is produced in this way by the time-base generator and which is directly dependent on the temperature. The voltage Vc across the capacitor 3 first increases in a known way in accordance with an inverse exponential function until the reference voltage Vr determined by the two resistors 4 and 5 has been reached. The capacitor 3 is then abruptly discharged and the capacitor voltage Vc also falls abruptly as a result. No special requirements are imposed on the variation with time of the capacitor voltage Vc. In particular, a linear increase in voltage, as in the case of a sawtooth voltage, is neither desirable nor required. Only the time intervals, that is to say the time differences t2–t1 or t3–t2 or t4–t3 etc. have to be unambiguously dependent on the prevailing temperature at constant operating voltage Vdd.

That flank of the capacitor voltage Vc which falls abruptly at the instants in time t1, t2, t3, t4 etc. is used to operate an electronic two-way switch 21 which functions in the same way as a flip-flop. As a result, switching takes place cyclically and continuously between two audio frequencies f1 and f2, the time duration of the tone prevailing in each case being a measure of the temperature to be measured. A similarly constructed temperature-dependent electronic two-way switch 21 is incorporated in the transponder TRS and forms the central component of the measuring device.

Figure 4:
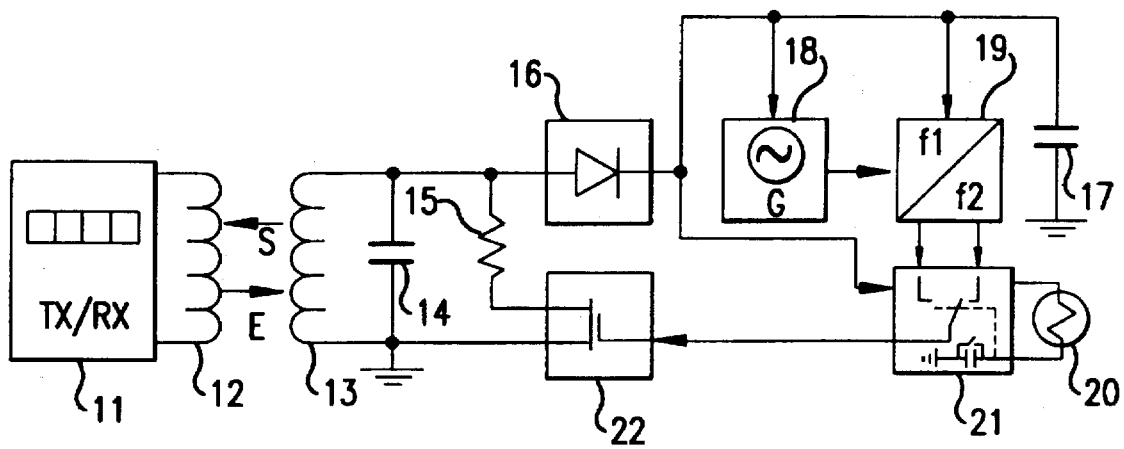
FIG. 4 shows an exemplary embodiment of the block diagram of the internal structure of a transponder for the temperature measurement.

FIG. 4 shows an embodiment of the block diagram of the internal structure of a transponder for temperature measurement. The operating power E made available by the interrogation field induces an alternating voltage in the resonant circuit comprising the transponder coil 13 and the capacitor 14. Said alternating voltage is converted by the rectifier unit 16 into a direct voltage which is required for operating the transponder and which is the operating voltage Vdd of the transponder TRS and is sufficiently smoothed by the capacitor 17. This smoothed, but distinctly unstabilized operating voltage Vdd is fed to the separate electronic components in the transponder for the purpose of supplying them. The audio-frequency generator 18 then produces a relatively low-frequency tone having the frequency f1, which increases with increasing values of the smoothed, but unstabilized direct voltage. The audio-signal generator 18 is therefore a freewheeling, that is to say unsynchronized, alternating-voltage generator, the frequency of the oscillations generated thereby depending on the operating voltage Vdd. If the output power of the transmitter of the transmitting and receiving unit 11 were to be kept constant, the frequency f1 of the low-frequency tone produced by the audio-frequency generator 18 in the transponder TRS would, in the case of a short distance between the transmitting/receiving coil 12 and the transponder coil 13, also be higher than would be the case at greater distances between the transmitting/receiving coil 12 and the transponder coil 13 because of the tighter coupling and the higher operating voltage associated therewith. On the other hand, the operating voltage Vdd in the transponder can easily be kept constant even with varying distances between the transmitting/receiving coil 12 and the transponder coil 13 if the output power of the transmitter of the transmitting and receiving unit 11 is controlled in such a manner that the low-frequency tone produced by the audio-frequency generator 18 is also constant with the frequency f1. For this purpose, the modulation signal produced by the transponder TRS must at least contain, accurately with respect to time, said low-frequency tone of frequency f1. So that it is possible to switch between different audio frequencies, a simple frequency converter 19 is connected downstream of the audio-frequency generator 18. Another, lower audio signal of frequency f2 is derived from the low-frequency audio signal having the frequency f1 produced by the audio-frequency generator 18. In order to differentiate the two audio signals having the frequencies f1 and f2, it is sufficient, in this connection, to halve or to divide by three the frequency f1 of the audio-frequency generator 18. The two audio signals having the frequencies f1 and f2 are both dependent on the operating voltage Vdd since they have, as common source, the audio-frequency generator 18 which is dependent on the operating voltage Vdd. Both audio signals are now fed to the temperature-dependent electronic two-way switch 21.

As a result of additional conversion ratios in the frequency converter 19, it is readily possible to derive further audio frequencies from the signal of the audio-frequency generator 18 and consequently to produce corresponding additional signals, for example in order to improve the synchronization. Since these are merely obvious further developments of the actual inventive idea, it has been decided not to provide a comprehensive elaboration thereof in order to keep the layout of the description clear.

The thermistor 20 has a certain resistance value as a function of temperature and consequently determines the time constant with which the temperature-dependent electronic two-way switch 21 switches continuously in cyclical sequence between the low-frequency audio signal having the frequency f1 and the lower audio signal f2 derived therefrom. The sequence generated in this way of alternating tones arrives at the input of the modulator unit 22, which is formed, for example, by a transistor said transistor is directly connected via a modulation resistor 15 to the resonant circuit comprising the transponder coil 13 and the capacitor 14. By driving the transistor in the modulator unit 22 in accordance with the sequence of the alternating tones, additional power is drawn by the resonant circuit, the modulation resistor 15 limiting the current consumption effected by the transistor in the modulator unit 22 and consequently reliably preventing the resonant circuit having to deliver, as a result of the modulation, so much energy that the operating voltage Vdd falls below a required minimum value below which the intended operation of the transponder TRS would no longer be ensured.

The rhythmic damping, effected by the transistor in the modulator unit 22 in accordance with the sequence of the alternating tones, of the resonant circuit formed by the transponder coil 13 and the capacitor 14 produces, as a result of the magnetic coupling to the transmitting/receiving coil 12, a signal S which is to be detected by the receiving section of the unit 11 and which is processed in a suitable manner by the signal processor of the unit 11. In particular the transmitting power of the unit 11 is so accurately controlled by the signal processor that the respective frequencies f1 and f2, at any rate the sound signal having the frequency f1 produced directly by the audio-frequency generator 18, is kept constant even in the case of a transponder moving in the interrogation field and, consequently, of different degrees of coupling so that the time difference between the changes in the respective tones depends solely and exclusively on the temperature and, consequently, an unambiguous value can be assigned thereto.

It is only then that calibration of the transponder, which still has to take place prior to its injection into the respective animal, is worthwhile. Calibration is preferably carried out by placing the transponder in a water bath at a known temperature of, for example, 40° C. The uncalibrated transponder is then activated in the water bath by a transmitter/receiver TRX. At the same time, the low-frequency audio signal produced directly by the audio-frequency generator 18 in the transponder TRS is adjusted to a specific value of, for example, 5 kHz by controlling the output power of the transmitter of the transmitting and receiving unit 11. The time interval of the cyclic switching during the sequence of alternating tones is determined and the corresponding value is stored. A relationship which can be reproduced as often as desired is now available between the temperature, on the one hand, the frequency f1, on the other hand, and the associated value of the time interval of the cyclic switching.

The transponder is thereby calibrated for this temperature value. For accurate measurements, other calibration points at other water bath temperatures should preferably also be determined.

The temperature is now measured very easily because, as the result of controlling the output power of the transmitting section of the transmitter/receiver TRX, the audio signal having the frequency f1, detected by the receiving section and originating from the audio-frequency generator 18 in the implanted transponder TRS, is tuned precisely to the value set during calibration. The time interval of the cyclic switching during the sequence of alternating tones is determined and processed, and the temperature is determined therefrom. The temperature values deviating from the calibration points can be determined with very good accuracy by mathematical approximation methods (for example, interpolation).

The transmitting and receiving unit 11 of the transmitter/receiver TRX is an extremely complicated apparatus which is equipped, in particular, with adequate computing capacity, which can be compared with the properties of a personal computer. This unit has memories for the calibrated data and for numerous pre-prepared programs for the systematic processing of the signals S emitted by the transponder TRS, for the control of the transmitting power and various interfaces for the data communication with other personal computers. However this is not a subject of the invention.

Figure 5:
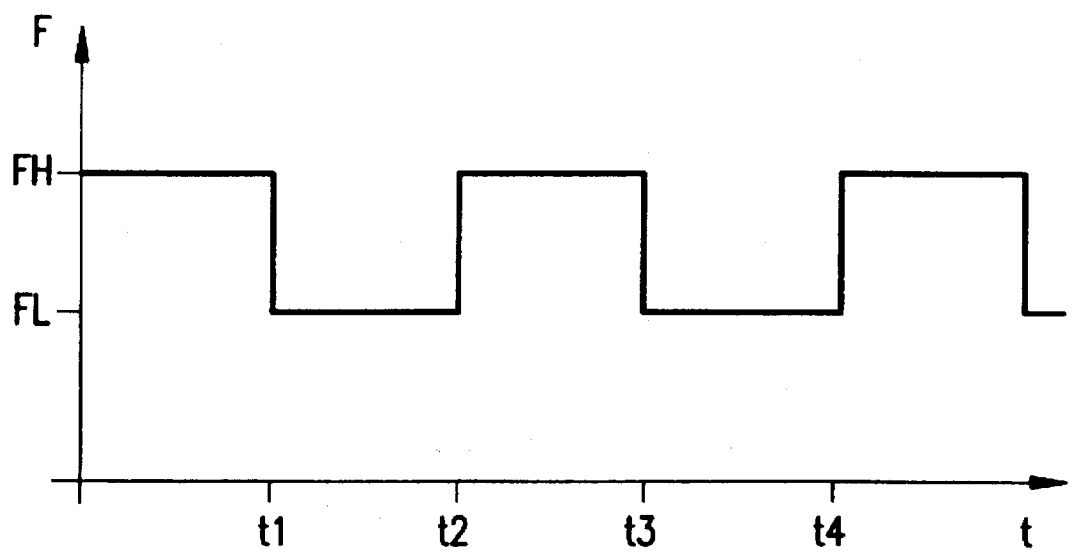
FIG. 5 shows, for the purpose of explanation, a typical pattern of the series of alternating tones obtained as a signal from the transponder at a certain, but constant temperature, the sequence of alternating tones occurring symmetrically.

FIG. 5 shows a modified pattern with time of the sequence of the alternating tones. The signal frequency F of the signal S produced by the transponder TRS is shown against time t. The tones having the frequencies FH and FL alternate with each other in a cyclically continuous manner. In this case, both the tone having the frequency FH and the tone having the frequency FL are derived from the low-frequency audio signal originating directly from the audio-frequency generator 18 of the transponder TRS by, for example, suitable division. The frequency f1 can be chosen to be higher by additional division of the frequency f1 of the audio signal derived directly from the audio-frequency generator 18. As a result, the resolution of the temperature to be measured is increased to 0.1° C. in the region of the body temperature of the animals. By choosing suitable division ratios, the frequencies FH and FL can be relatively close to one another. For example f1 is divided by 10 and FH is produced and it is divided by 11 and FL is produced. As a result, the bandwidth needed for the receiver of the transmitting and receiving unit 11 of the transmitter/receiver TRX is very small. As a result of the reduced bandwidth, the signal S emitted by the transponder TRS can still be filtered out of the noise level even at greater distance.

Figure 6:
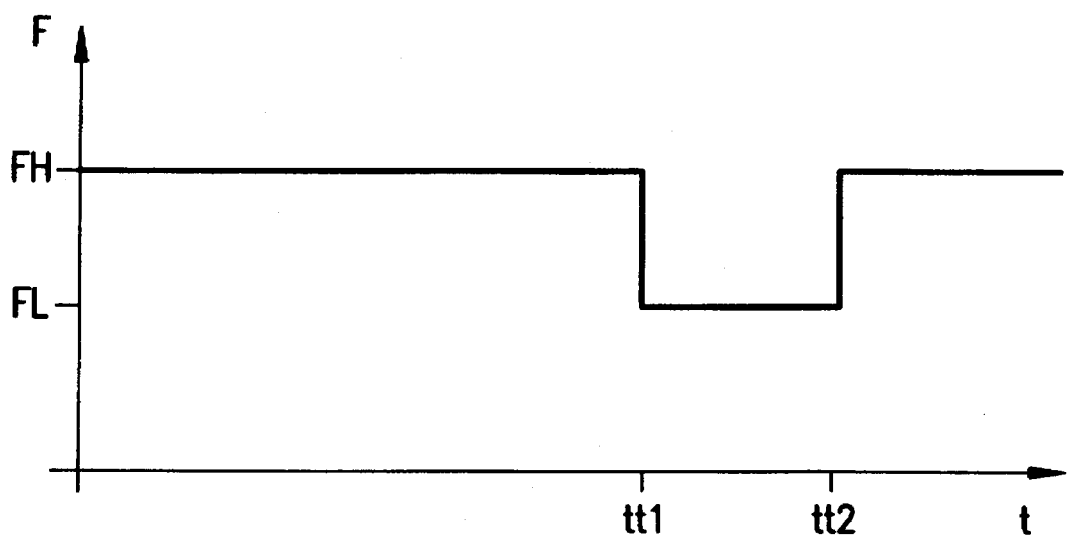
FIG. 6 shows, for the purpose of explanation, a typical pattern of the sequence of alternating tones obtained as a signal from the transponder at a certain, but constant temperature, the sequence of the alternating tones being asymmetrical.

FIG. 6 shows a further variant of the signal S emitted by the transponder TRS in the form of another sequence of alternating tones. In this case, not every separate falling flank of the voltage Vc of the capacitor 3 (FIG. 2) is used to control the temperature-dependent electronic two-way switch 21, but only the third and fourth, seventh and eighth etc. The time difference tt2–tt1 is precisely identical to the time intervals t2–t1, t3–t2, t4–t3 etc. used for the temperature measurement as described above. The prevailing temperature can consequently again be determined accurately.

The modulation phase in which the transponder TRS produces an audio signal having the frequency FH as signal S is now, however, markedly longer because of the asymmetry deliberately provided in the sequence of alternating tones. As a result, the reference frequency FH determined in a meaningful way during the calibration can be set more easily and more accurately, as a result of which the measurement accuracy is significantly increased.

FIG. 7 shows the further variant of the signal S emitted by the transponder TRS in the form of yet another sequence of alternating tones. In this case, a relatively fast alternation also additionally takes place, for example, between two predetermined tones, FH and FL, in a further modulation phase. As a result of the predetermined sequence of the tone alternation, additional information, such as identification numbers which have been previously programmed into a memory M of the transponder TRS to be injected, can be transmitted in a form thus coded.

In contrast to the digital modulation method conventionally used in information technology and having a frequency change (FSK), the appreciably higher carrier-wave frequency is not modulated in this case, but sinusoidal signal tones which persist for a sufficiently long time and which characteristically also have different lengths are generated in addition to the carrier-wave frequency signal. As a result, high transmission speeds for data transmission are not possible, but then they are not required in this case.

By means of an additional, supplementary modulation phase, it is also possible to add, in addition, further audio frequency changes having, for example, always exactly predetermined time duration as synchronizing or control signals, as a result of which the reliability of the processing of the signals S in the transmitter/receiver TRX can be improved still further.

In this connection, it is advantageous to use more than two different audio frequencies. It is only of importance that the additional signals are also always derived from the common voltage-dependent audio-frequency generator 18.

The incorporation of an additional memory unit 23 in the transponder TRS for producing additional modulation signals in accordance with the information stored in an electronic memory M is depicted in FIG. 8. The signal from the temperature-dependent electronic two-way switch 21 is not fed directly to the modulator unit 22, but first arrives in the memory unit 23. First, only the alternating audio signal is allowed through and is able to reach the modulator unit 22 unimpeded. At the same time, the memory unit 23 checks with the aid of a simple flank detector the activities of the temperature-dependent electronic two-way switch 21 and 'sees' from the falling frequency at the instant in time tt1 and the frequency which again increases at the instant in time tt2 or the associated falling flanks of the voltage Vc of the capacitor 3 that the information required for the temperature measurement has already arrived in the modulator unit 22.

At this instant in time, for example, the thermistor 20 is briefly switched off and the memory unit 23 in turn transmits, depending on the information previously stored in the memory M, suitable signals, coded as desired, to the electronic two-way switch 21.

After all the stored information has been emitted, the thermistor 20 is again switched on and the measurement cycle already described is continued again.

All the transponders TRS operated in conjunction with the measuring device are externally supplied, that is to say they do not need additional power sources for their intended operation, that is to say no built-in batteries. As a result, the transponders TRS are only activated when the animal which is carrying around with it a transponder TRS injected by means of a hollow needle, has approached the transmitting/receiving coil 12 closely enough for the power E obtained by the transponder TRS from the interrogation field to be sufficiently high. For this purpose, the animals have to approach the transmitting/receiving coil 12 to within less than approximately 1 metre. It is therefore preferable to position the generally stationarily mounted transmitting/receiving coil 12 at a point where the animals appear several times a day. Suitable points are feeding points and drinking points.

It is, however, also possible to construct portable transmitters/receivers TRX. In that case, ferrite aerials are then effective as transmitting/receiving coil 12. The respective animal can be approached therewith and wire-free information obtained about the body temperature, identity etc.

If the transponder is not activated by an interrogation field, it does not emit any interfering signals either and it does not consume any current either. As a result, the transponder can remain in the respective animal throughout its entire life. The transponder does not have to be monitored and no batteries have to be replaced either. The life of the transponder is therefore virtually unlimited compared with the life of other electronic apparatuses. The only harm done to the animal is a short pain during the once-off injection, such as the animal knows from vaccinations. After that, it will not be necessary to disturb the animal again in order to take manual temperature measurements in the region of the anus. In this respect, the measuring device is also a contribution to the correct husbandry of useful animals and breeding animals.

I claim:

1. A measuring device comprising:
   at least one transponder including:
      a temperature sensor;
      a temperature to frequency converter controlled by said temperature sensor;
      a transceiving coil for generating an unstabilized voltage from an interrogation field;
      a frequency generator supplied with said unstabilized voltage, for generating a frequency based on said unstabilized voltage;
      a frequency converter for producing at least two different frequencies based on the frequency generated by said frequency generator, said temperature to frequency converter switching between said at least two different frequencies;
   a modulating unit controlled by said at least two different frequencies for modulating the interrogation field; and
   a transceiver for generating an interrogation field including means for determining the measured temperature from the modulated interrogation field based on the time duration of an interval of one of said at least two frequencies,
   wherein the transmitting power of the transceiver is controlled on the basis of one of said at least two frequencies being present in the modulated interrogation field such that said unstabilized voltage is kept constant.

2. A measuring device according to claim 1, wherein said transponder further comprises a memory for modulating the sequence of said at least two frequencies, produced by said frequency converter and switched by said frequency generator, in a predetermined manner based on the information programmed into said memory.

3. A measuring device according to claim 2, wherein said information relates to an identification number.

4. A measuring device according to claim 1, wherein the transponder further modulates the interrogation field by further frequency changes each having a predetermined time duration.

* * * * *